United States Patent

Huddart et al.

[11] Patent Number: 5,640,951
[45] Date of Patent: Jun. 24, 1997

[54] HUMIDIFIER CONDUIT

[75] Inventors: Brett John Huddart; Ilija Orec; Andrew Paul Maxwell Salmon, all of Auckland, New Zealand

[73] Assignee: Fisher & Paykel Limited, Auckland, New Zealand

[21] Appl. No.: 404,420

[22] Filed: Mar. 15, 1995

[30] Foreign Application Priority Data

Mar. 15, 1994 [NZ] New Zealand .............. 260099
Dec. 15, 1994 [NZ] New Zealand .............. 270143

[51] Int. Cl.⁶ .................................................. A61M 16/00
[52] U.S. Cl. .......................... 128/204.77; 128/203.26; 128/911; 138/129
[58] Field of Search .................. 128/200.24, 201.13, 128/16, 17, 203.26, 27, 204.17, 18, 207.14, 911, 912; 138/129

[56] References Cited

U.S. PATENT DOCUMENTS

| | | |
|---|---|---|
| 4,051,847 | 10/1977 | Henkin . |
| 4,172,474 | 10/1979 | Stahl . |
| 4,336,798 | 6/1982 | Beran . |
| 4,498,473 | 2/1985 | Gereg ................. 128/207.15 |
| 4,531,551 | 7/1985 | Eichelberger et al. . |
| 5,143,060 | 9/1992 | Smith . |
| 5,259,418 | 11/1993 | Hamrick ................. 138/104 |
| 5,357,948 | 10/1994 | Eilentropp ............. 128/204.17 |
| 5,377,670 | 1/1995 | Smith ..................... 128/204.17 |

FOREIGN PATENT DOCUMENTS

| | | |
|---|---|---|
| 0201985 | 11/1986 | European Pat. Off. . |
| 0579384 | 1/1994 | European Pat. Off. . |
| 0621050 | 10/1994 | European Pat. Off. . |
| 2505658 | 11/1982 | France . |
| 0332481 | 9/1989 | France . |
| 3730551 | 3/1989 | Germany . |
| 4244493 | 12/1992 | Germany . |
| 704819 | 3/1954 | United Kingdom . |

*Primary Examiner*—Vincent Millin
*Assistant Examiner*—Robert N. Wieland
*Attorney, Agent, or Firm*—Trexler, Bushnell, Giangiorgi & Blackstone, Ltd.

[57] ABSTRACT

A humidifier conduit has an enclosed helical passageway in the wall thereof to provide an insulating barrier against heat transfer from the inside of the conduit to the outside of the conduit. The conduit may include at least one heating means hectically disposed between the inner wall and outer wall of the conduit to assist in the retention of a desired gases temperature in the humidified air flow which is to flow through the conduit in use. The conduit preferably is constructed by helical winding of a unit profile and bonding of adjacent turns of the helically wound profile to form the conduit, the unit profile including complementary connecting means so that adjacent turns of the helically wound profile are securely connected to form the conduit. The unit profile may include an overlapping member to overlap adjacent turns of the profile and act in an armadillo-like fashion to ensure flexibility of the conduit, while retaining the insulative properties of the double wall and enclosed helical passageway.

28 Claims, 5 Drawing Sheets

HUMIDIFIER CONDUIT

BACKGROUND TO THE INVENTION

1. Field of the Invention

This invention relates to respiratory humidifiers and more particularly though not solely to respiratory humidifier conduits used in the breathing circuits of humidifiers to provide humidified gases to a patient or other person in need of such gases.

2. Description of the Prior Art

It is well known that, in an attempt to minimise or eliminate "rain out" or condensation occurring within a respiratory breathing circuit, heating elements have been used to maintain a desired temperature for the gases and the inner conduit walls. The temperature of the gases within the humidifier, when delivered to the patient, is typically 37° C. and, room temperature is typically in the vicinity of 22° C. The heating element has been provided around the outer surface of the conduit so that the heat dissipated by the element is conducted through the conduit wall to heat or maintain the temperature of the gases flowing within the conduit. Respiratory humidifier conduits including heating elements enable the gas delivered by the conduit to be liquid free and of high relative humidity.

Originally, in order to overcome the problem of condensation within the conduit, "water traps" comprising special dishes connected at the mid point of the conduit were used to collect any liquid which may have condensed within the conduit. It is obvious that the use of such a device depends on gravity causing the liquid to flow to the water trap rather than to the patient.

Recently, respiratory conduits have included heater wires external of or even within the conduit. There are major disadvantages associated with providing a heater wire within the conduit. These disadvantages include the additional resistance to the gas flow, impairing the capability of the ventilator which controls the pressure and volume of gases delivered to the patient and cleaning is greatly impaired. When the gases flowing in the conduit are combustible gases such as some gases used in anaesthesia, there is a potential for a fault in the heating element causing sparking which could ignite the gases.

An example of a respiratory humidifier conduit having a heating wire disposed within the conduit is disclosed in Bain U.S. Pat. No. 3,856,051. For the foregoing reasons this arrangement is undesirable.

An example of a respiratory humidifier conduit having heating wires attached external to the conduit is disclosed in German Patent Application No DE 42 44 493. The respiratory humidifier conduit disclosed consists of a cylindrical conduit having spirally wound thereon a rib or ridge which structurally supports the conduit walls acting to prevent kinking of the tube. Heating conductors are positioned either along the ribs or ridges on the outside of the tube or within the ribs or ridges (if the ribs or ridges are tubes wound around the conduit). The respiratory humidifier conduit has the disadvantage that the heating conductors at the base of the ribs or ridges dissipate much of their energy to ambient air. Also, due to its construction, the respiratory conduit disclosed is not supple or easily bent and therefore ill suited to use in conditions which require the conduit to be manipulated to a different shape depending on the individual circumstances of the person requiring the humidified gases. In addition the conduit disclosed is very heavy.

It is, therefore, an object of the present invention to provide a respiratory humidifier conduit which goes some way towards overcoming the above disadvantages or which will at least provide the public with a useful choice.

BRIEF SUMMARY OF THE INVENTION

In one aspect of the invention may broadly be said to consist in a conduit for carrying humidified gases comprising:

at least one axially extensive unit profile helically wound with adjacent turns touching to define an axial passage within said helix, said unit profile when helically wound, with adjacent turns touching, defining at least one enclosed helical passage, around said axial passage, each turn of said helically wound profile bonded to adjacent turns of said profile.

In a further aspect the invention may broadly be said to consist in a process for manufacturing a humidified gases conduit comprising the steps of:

forming an axially extensive unit profile, said unit profile when helically wound with adjacent turns touching, defining at least one helical passage, helically winding said axially extensive unit profile such that said profile forms the wall of a conduit, one surface of said profile forming the internal surface of said conduit, an opposite surface of said profile forming the external surface of said conduit, and bonding adjacent turns of said helically wound unit profile.

In a still further aspect the invention may broadly be said to consist in a conduit for carrying humidified gases comprising:

an inner wall defining the gases flow conduit an outer wall co-axially located with respect to said inner wall, said outer wall spaced radially outwardly from said inner wall at least one intermediate co-axial helical wall disposed between said inner wall and said outer wall, said inner wall, said outer wall and said intermediate wall together defining at least one helical passage around said inner wall, and a heater element disposed between said inner wall and said outer wall and spirally around said inner wall.

The invention consists in the foregoing and also envisages constructions of which the following gives examples.

BRIEF DESCRIPTION OF THE DRAWINGS

Preferred forms of the present invention will now be described with reference to the accompanying drawings in which.

DETAILED DESCRIPTION

Figure 1:
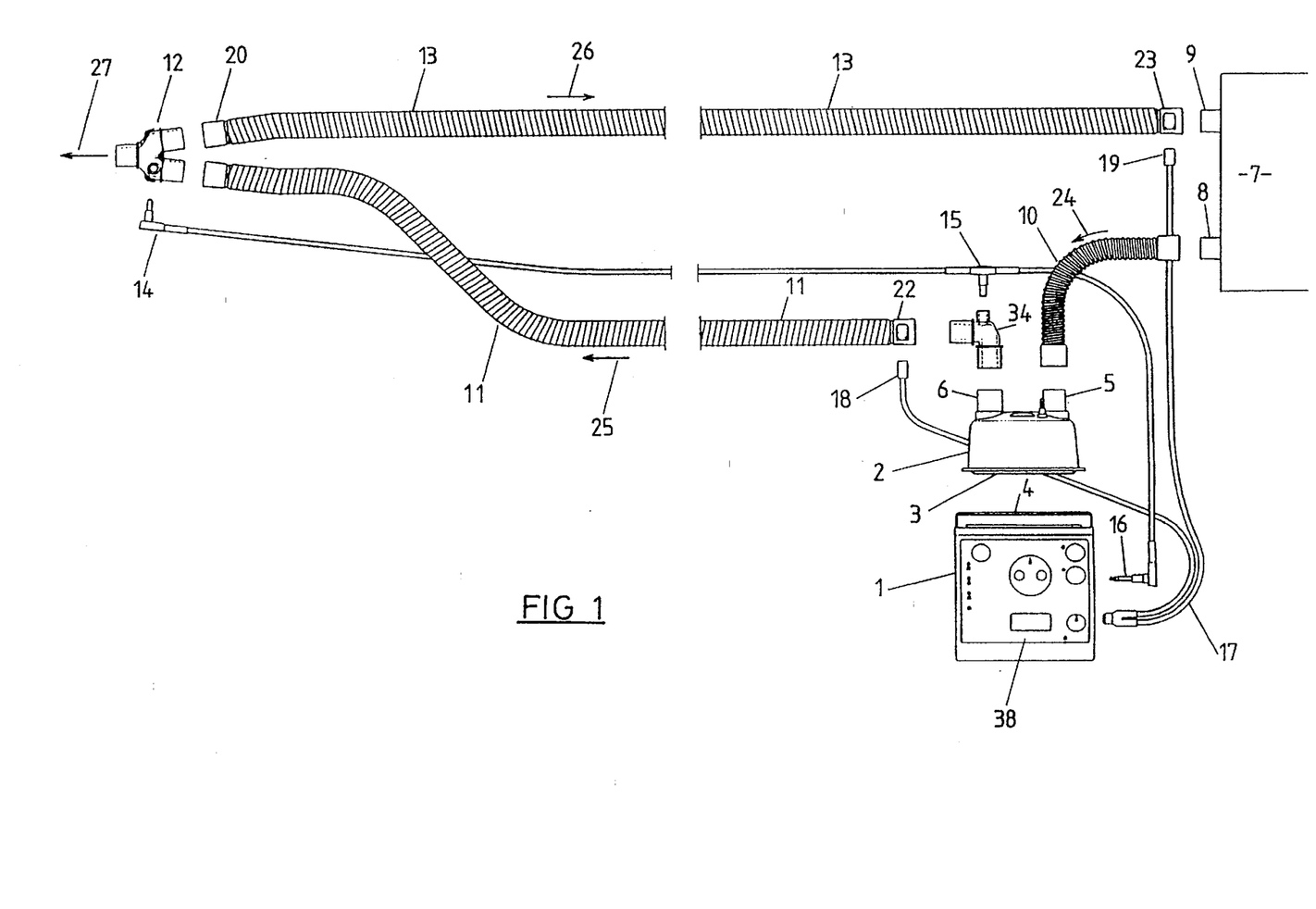
FIG. 1 is an exploded schematic view of a humidification system incorporating the respiratory humidifier conduit of the present invention.

With reference to FIG. 1 a respiratory humidification system is shown wherein respiratory humidification conduits 11 (inspiratory line) and 13 (expiratory line) are used to provide humidified gases from a humidifier 1 to a patient or other person in need of such gases. The humidifier 1 is provided with a heating plate 4 which is controlled by the humidifier 1 to heat water within a humidification chamber 2 having a heat conducting base 3 which, in use, sits on the heating plate 4. The humidification chamber 2 has an inlet 5 to receive gases (which may be for example air, oxygen or an anaesthetic gas) via a connecting conduit 10 supplying gases from a ventilator 7 through ventilator outlet 8.

The humidification chamber 2 has an outlet 6 through which the gases supplied by the ventilator (and which have been humidified) pass into the inspiratory conduit 11 via connecting piece 34. The ends of the inspiratory conduit 11 are terminated in cuffs 21 and 22. Cuff 22 has electrical connecting pins moulded therein for a connection to heater wire plug 18 which supplies power from a controlled power supply within humidifier 1 through heater power wire 17. A resistive heater element is incorporated in the conduit 11 as will soon be described and which is connected to the above mentioned connecting pins within cuff 22. The conduit cuff 21 is connected to a Y shaped adaptor 12 having an outlet for the humidified gases to flow in the direction of arrow 27 to the patient or other person in need of such gases.

The Y shaped adaptor 12 has a further outlet for connection to cuff 20 of an expiratory conduit 13 which is further connected to the inlet 9 of ventilator 7 by cuff 23. Cuff 23 is similar to cuff 22 as it also has a connection for a heater wire which is incorporated in conduit 13. A further heater wire plug 19 supplies power to the further heater wire within the conduit 13 via connection to the connecting pins in cuff 23 through heater power wire 17.

Preferably the humidification system incorporates the ability to sense temperatures at various positions along the path of the gases within the system. A first temperature probe 14 is provided for insertion within an orifice in the Y shaped adaptor 12 in the path of the inspiratory gases so that the temperature of the gases at the point they are supplied to the patient may be determined and fed back to the humidifier 1. The humidifier 1 includes control means 38 which controls the temperature and/or the on/off state (or duty cycle) of the heater plate 4. Controller 38 could, for example, comprise a microprocessor programmed to carry out the operation of the humidifier as herein described.

A further temperature probe 15 is provided directly at the humidification chamber outlet 6 by insertion within connecting piece 34 so that the temperature of the gases leaving the humidification chamber may be fed back to the control circuitry within the humidifier 1. The control means 38, as well as controlling the heating of the water within the humidification chamber, also controls the supply of power to the heater wires within conduits 11 and 13. Arrows, 24, 25 and 26 demonstrate the direction of flow of the gases from the ventilator through the humidification chamber 2, to the patient in the direction of arrow 27 and then back along the expiratory conduit 13 to the ventilator 7.

Figure 2:
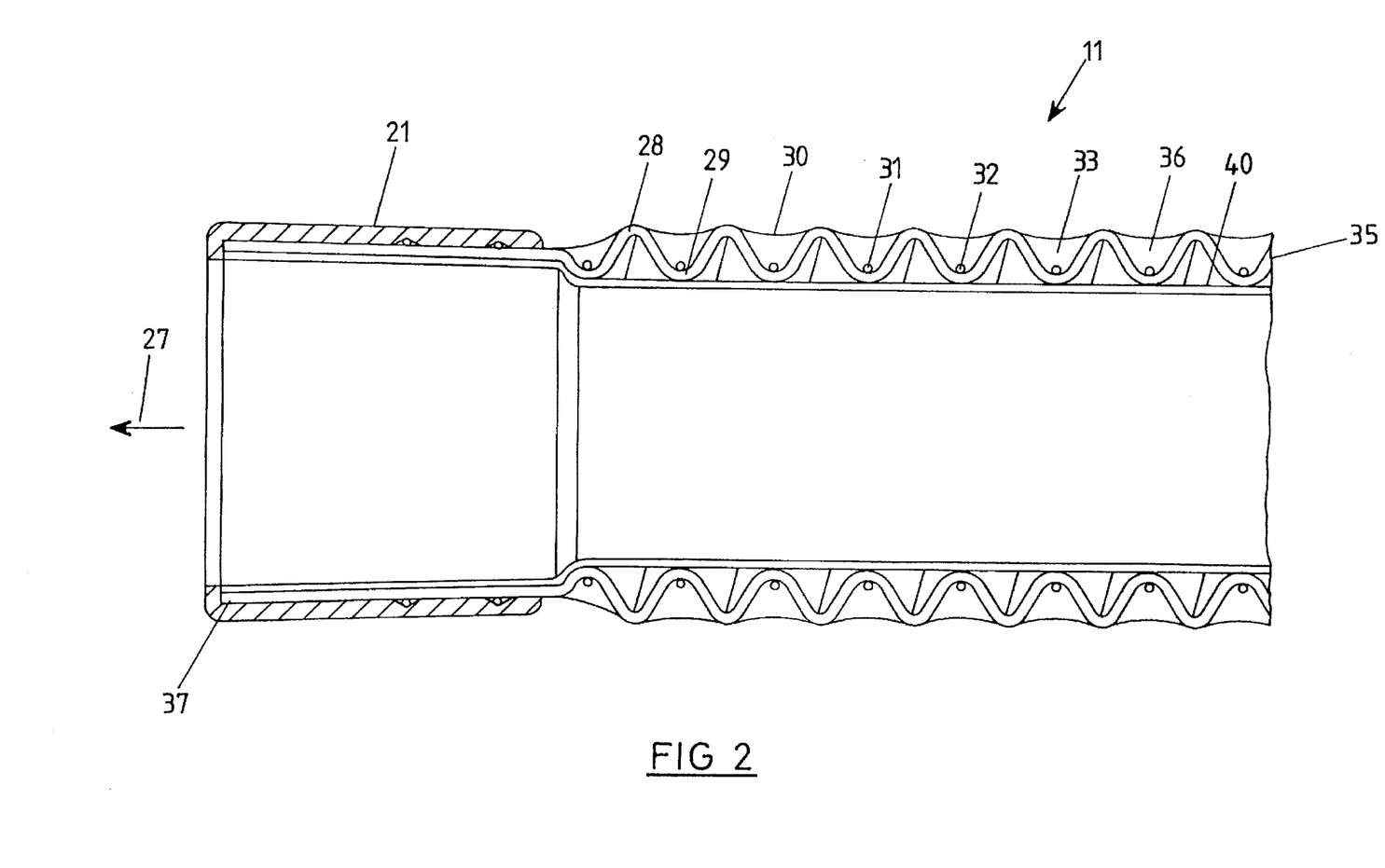
FIG. 2 is a cross sectional view of a section of the respiratory humidifier conduit shown in FIG. 1, according to a first embodiment of the present invention.

With reference now to FIG. 2, one of the conduits, in this case inspiratory conduit 11, is shown in cross-section in more detail than in FIG. 1. It can be seen that the conduit 11 comprises an inner corrugated conduit 35 surrounded by an outer sheath 30. Both the outer sheath 30 and inner corrugated conduit 35 are preferably extruded in a flexible plastics material, for example AT 1080 (which is a compound consisting of polyethylene and EVA and is manufactured by Imperial Chemical Industries (ICI)). Although the inner conduit 35 appears corrugated in cross-section, this is as a result of the outer surface of inner conduit 35 having impressed therein two equally pitched and equally spaced helical grooves along the entire length of the conduit. In cross-section the grooves may be considered to be made up of a ridge 28 followed by a groove 29. The outer sheath 30 is much thinner in comparison to the thickness of inner conduit 35 (being approximately 100 μm to 150 μm thick) and may be extruded directly onto the inner conduit 35 during manufacturing.

The conduit further includes inner sheath 40 which may also be extruded from for example AT1080. Inner sheath 40 is disposed internal of corrugated conduit 35, and bonds to the internal side of the troughs of grooves 29 producing further airpockets 41 and 42 between the corrugated conduit 35 and the inner sheath 40. Like the outer sheath 30 inner sheath 40 is preferably of significantly lesser thickness than the thickness of corrugated conduit 35.

The outer sheath 30 bonds to the inner conduit 35 around the crests of ridges 28 producing air pockets 33 and 36 which are helical pockets of air surrounding the inner conduit 35. Within the pockets of air 33 and 36, heating means, for example heater wires 31 and 32 are provided spirally wound within the grooves at or near the base of the grooves 29, along the length of the conduit. The wires are wound around the inner conduit 35 before the addition of the outer sheath 30. The end 37 of the conduit is terminated in a cuff 21 which seals the outer sheath 30 to the inner conduit 35 at the end of the conduit in addition to providing a connecting termination for heater wires 31 and 32. The other ends of the heater wires 31 and 32 are separately terminated within cuff 22 to respective connecting pins for connection to heater wire plug 18. An example of a material which may be used as a heater wire is nichrome. The choice of resistance per unit length for the heater wire is dependent upon the length of conduit under manufacture.

It would alternatively be possible to wind the inner conduit 35 with one individual heater wire by winding the heater wire down one of the helical grooves to the end 37 of conduit 35, then crossing the wire into the other helical groove so that the wire may be wound back to the starting end of the conduit.

Alternatively a single rather than double helix could be used, one heater wire provided in the helical pocket formed between the corrugated conduit 35 and the outer sheath 30, and one heater wire provided in the helical pocket formed between corrugated conduit 35 and the inner sheath 40. However this is not a preferred configuration as the wire positioning is not fully controlled, and the presence of a wire against inner sheath 40 may damage the inner sheath 40.

An alternative to having both heated wire 31 and 32 of high resistance, producing heat, it is advantageous that instead one of the heater wires is of high resistance, and one of the heater wires is of substantially no resistance, so that with the patient end of the high resistance wire connected to the patient end of the lower resistance wire, the heater wires may be connected to a power source, for example a 12 V or 24 V DC supply such that the voltage along the high resistance wire ranges substantially from the supply voltage at the supply end to substantially zero volts at the patient end, and the low resistance return wire is at substantially zero volts along its entire length. This provides some advantages, in particular it has the benefit of low electromagnetic radiation close to the patient.

Figure 9:
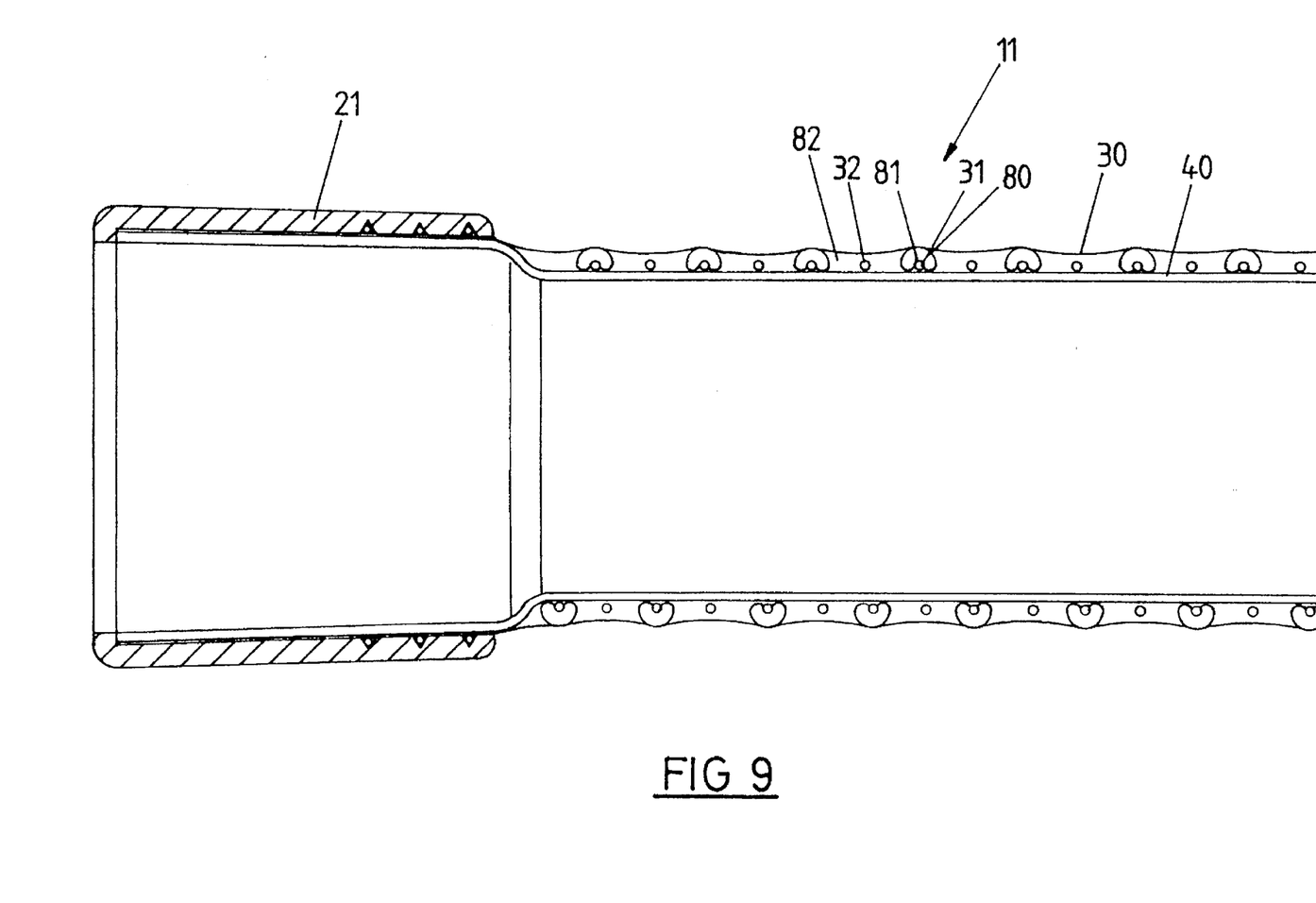
FIG. 9 is a cross-sectional view of a section of the respiratory humidifier conduit shown in FIG. 1 according to a third embodiment of the present invention.

Referring to FIG. 9, an alternative embodiment of the present invention is shown in which inner sheath 40 and outer sheath 30 are separated by elongate narrow member 80 wound helically around inner sheath 40, the inner sheath, outer sheath and elongate member therefore defining helical passageway 82 which spirals around the inner sheath 40. A heater wire, for example 32, may be located in the thus formed helical passageway. Elongate member 80 preferably has axial groove 81 formed therein, and the heater wire is then preferably disposed in the groove 81, as shown by heater wire 31 so that the heater wire is disposed against the inner wall 40 to thereby improve the heating efficiency of the heater element. Preferably as shown to aid in placing the elongate member 80, elongate member 80 has a flattened portion adjacent the inner wall 40. Preferably as described above, one of heater wires 31 and 32 is of substantially higher resistance than the other, in this case the wire of higher resistance preferably being wire 31 disposed in the axial groove 81.

Manufacture of the conduit of FIG. 9 is preferably conducted by extruding the inner wall 40, the elongate member 80 and the outer sheath 30 simultaneously. The heater wire 31 may be disposed inside or at the surface of member 80 during the extrusion process.

Figure 3:
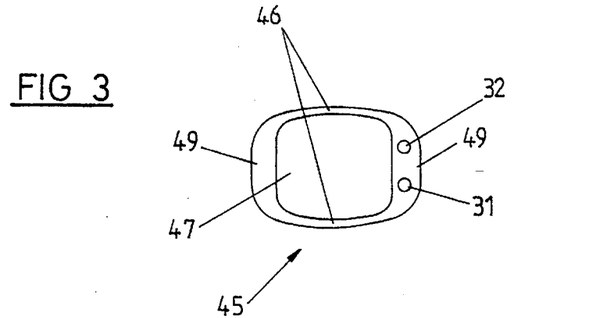
FIG. 3 is a cross-sectional view of the axially extensive unit profile of a second embodiment of the present invention.
Figure 4:
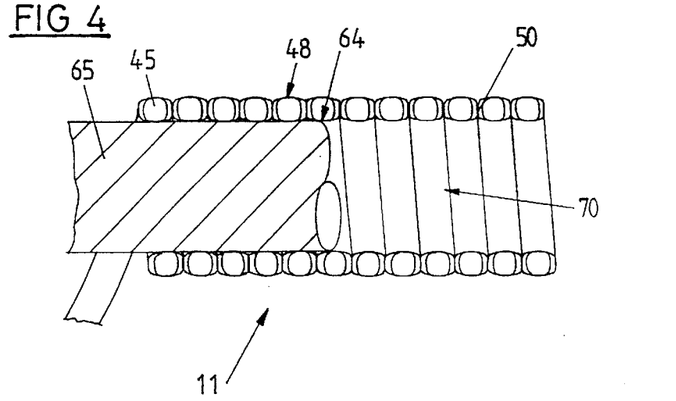
FIG. 4 is a cross-sectional view of the humidifier conduit constructed using the axially extensive unit profile of FIG. 3.

With reference to FIGS. 3 and 4, a further alternative embodiment of the present invention is shown in which conduit 11 is formed by forming an axially extensive unit profile 45, helically winding unit profile 45 so that unit profile 45 forms the wall of a tube, the passage 70 of the tube being coaxial with the axis of the helix and bonding adjacent turns of the helically wound unit profile 45. It is considered that the most appropriate method of forming unit profile 45 is by extruding a flexible plastic section, for example using the aforementioned material AT1080, and that the spiral winding of the axially extensive unit profile 45 can be performed by for example winding the unit profile about cylindrical member 65. With reference to FIG. 3 it can be seen that unit profile 45 comprises a tubular section having axial internal cavity 47, surrounded by, on two sides, opposing thin walls 46, and on the other two sides opposing thicker walls 49. Unit profile 45 also includes two heater wires 31 and 32 which may for example be located in the unit profile 45 during the extrusion of unit profile 45.

Referring to FIG. 4, axially extensive unit profile 45 is shown helically wound about tubular member 65, to form tube 11. As it is shown, the opposing thinner walls 46 form the internal 64 and external 48 surfaces of the tube 11. Opposing thicker walls 49, when unit profile 45 has been helically wound, become adjacent in adjacent turns, and adjacent outer surfaces of walls 49 are bonded, for example at join 50. This joint may be made most commonly with an adhesive, however other forms of bonding are available, for example thermal welding using a laser or an eddycurrent heatable ferrous filament disposed in the unit profile, to melt one or both adjacent surfaces, cooling of the surfaces resulting in a bonded joint 50. The tubing 11 thus formed has significant advantages, for example enclosed airspace 47 entrapped between inner conduit surface 64 and outer conduit surface 48 lends very good insulative properties, thereby reducing heat loss between the heated gases flowing in conduit 11 and the cooler ambient exterior atmosphere when in use. Further, the tubing, with evenly spaced spirally wound heater wires 31 and 32, provides even heating, or heat maintenance of the gases flow. The conduit 11 also has the further advantage that both the interior and exterior surfaces are substantially smooth and therefore have a lower heat transfer rate than many currently used conduits where corrugations, designed to allow flexibility in the conduit, can act as cooling fins and often facilitate unwanted heat transfer. In order to maintain flexibility in the tube 11, the unit profile 45, as described, has thinner walls 46. Thinner walls 46 are easily able to buckle, and thereby allow the longitudinal wall elasticity necessary for bending and flexing of the tube 11.

Figure 5:
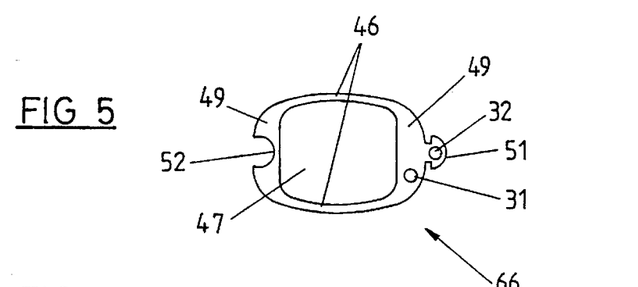
FIG. 5 is a cross-sectional view of a variant of the axially extensive unit profile shown in FIG. 3.
Figure 6:
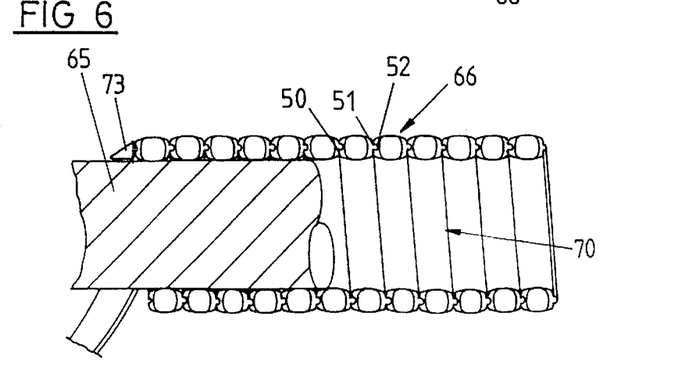
FIG. 6 is a cross-sectional view of the humidifier conduit formed using the axially extensive unit profile of FIG. 5.

With reference to FIGS. 5 and 6, a variant of the embodiment of the invention shown in FIGS. 3 and 4 is depicted, in which the bonding of adjacent turns of the helically wound unit profile 66 is, preferably in addition to adhesive or thermodynamic bonding, assisted by the provision on unit profile 66 of female connection means 52 and male connection means 51, the male connection means 51 of one turn of helically wound unit profile 66, being engaged with the female connection means 52 of the adjacent turn of helically wound unit profile 66. In this embodiment it can again be seen that heater wires 31 and 32 are provided in the unit profile 66. It is considered preferable, as shown in the FIG. 5, that heater wire 32 is disposed in the male connection means, so that thermoplastic bonding of adjacent turns of the unit profile may be accomplished by the passing of a high current through the heater wire 32, thereby locally melting the surrounding plastic of at least the male connection means, cooling of the molten plastic causing bonding. Given the possible detrimental effect that excessive currents may have on the heater wire 32, it is instead possible that rather than disposing heater wire 32 in male connection means 51, a third wire might be used.

Figure 7:
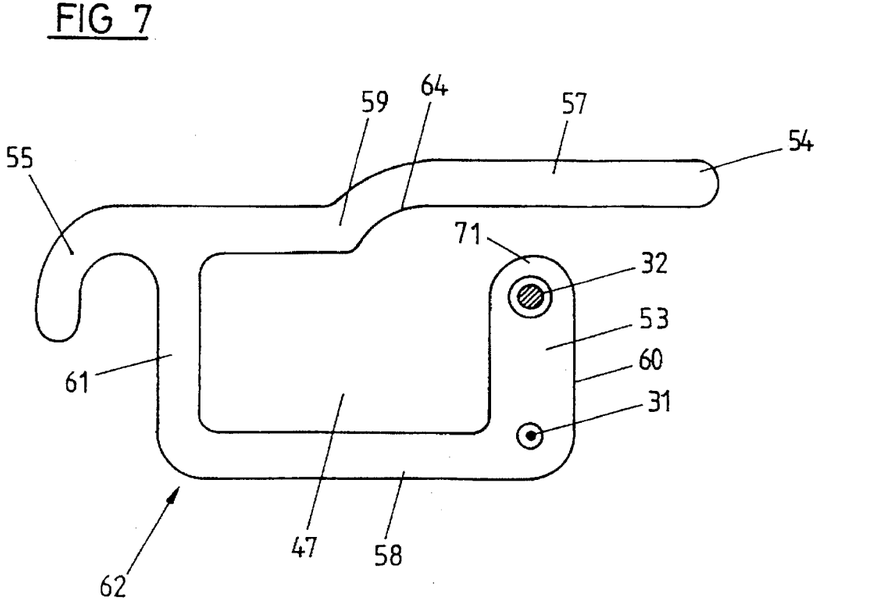
FIG. 7 is a cross-sectional view of another variant of the axially extensive unit profile of FIG. 3.
Figure 8:
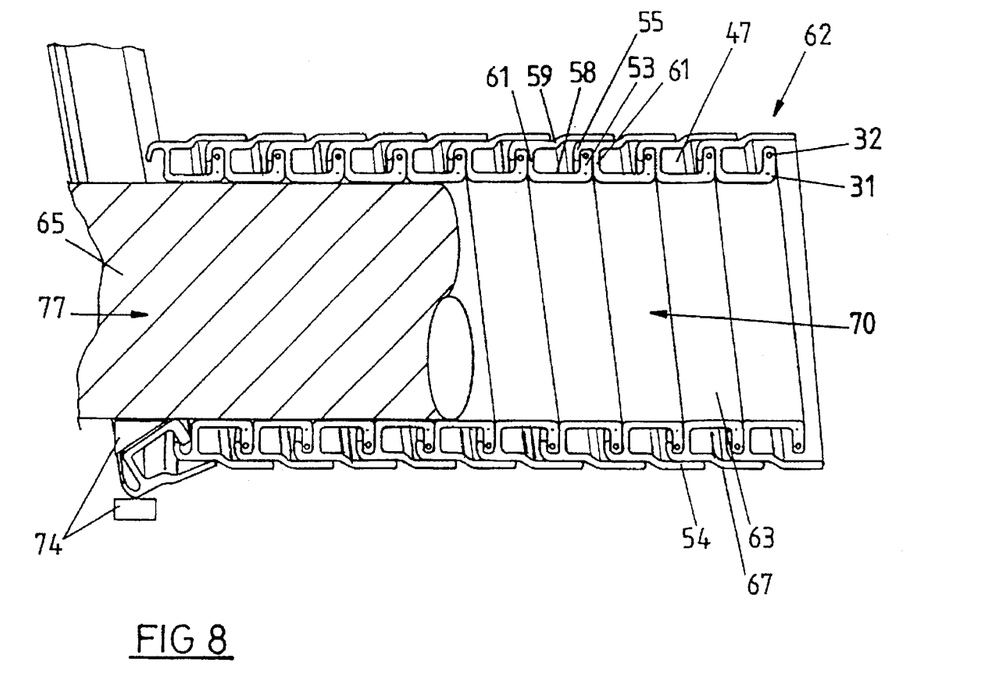
FIG. 8 is a cross-sectional view of the humidifier conduit formed using the axially extensive unit profile of FIG. 7.

With reference to FIGS. 7 and 8, a further variant of the embodiment shown in FIGS. 3 and 4 is depicted, having unit profile 62. Unit profile 62 varies somewhat from unit profile 45 and from unit profile 66.

Rather than relying on the buckling of walls 46 as in FIGS. 3 and 5 to provide flexibility for the humidifier conduit, unit profile 62 relies on armadillo-like plates or scales formed by overlapping portion 57 to provide flexibility for the humidifier conduit. As shown in FIG. 7, unit profile 62 preferably comprises inner wall 58 and outer wall 59, which is substantially parallel to inner wall 58, both walls extending from opposite ends of a connecting wall 61 perpendicular to both inner and outer walls 58 and 59. A helically wound unit profile of this simplified form, with the free end of inner wall 58 of the axially extensive unit profile bonded in the helically wound form to the outer surface of connecting wall 61, forms enclosed helical cavity 47. As shown in FIG. 8, cavity 47 is surrounded on its four sides by outer wall 59, inner wall 58 and connecting wall 61 of one turn of the axially extensive unit profile, and on the fourth side by connecting wall 61 of an adjacent turn of the axially extensive unit profile.

As shown in FIGS. 7 and 8, the bonding of adjacent turns of the helically wound axially extensive unit profile can be facilitated and enhanced by provision on the unit profile 62 of bonding wall 53, disposed from the end of inner wall 58 opposite to the connection between inner wall 58 and connecting wall 61, and parallel to connecting wall 61, so that the exterior surface 60 of bonding wall 53 may be bonded for example by adhesive to the exterior surface of connecting wall 61. As shown in FIG. 7, bonding wall 53 may extend only partially between inner wall 58 and outer wall 59, however if only adhesive bonding is to be used, then it would be preferable that bonding wall 53 extend fully from inner wall 58 to a point adjacent outer wall 59. In the embodiment shown in FIG. 7 however, further means to facilitate the secure connection of adjacent turns of the wound unit profile are shown. Hooking wall 55 is provided at the outer end of connecting wall 61. When the unit profile is wound, the hooking wall 55 hooks over the free end 71 of bonding wall 53 to further secure adjacent turns, and therefore hooking wall 55 is preferably formed with internal curvature complementary to the thickness of bonding wall 53. As with the supplementary connection means 51 shown in FIG. 5, it is possible to provide in bonding wall 53, electrically resistive wire 32 which, with the unit profile helically wound and hooking wall 55 engaged over the end 71 of bonding wall 53, may have a substantial current passed through it, to cause the wire 32 to heat and preferably locally melt the material of which the bonding wall 53 and hooking wall 55 are formed, and therefore form an integral bond between the hooking wall 55 and the bonding wall 53. The embodiments shown also include heater wire 31.

As shown in FIG. 7, it is preferable that the outer wall 59 of unit profile 62 has curvature 64 to step out the outer wall 59 so that a smooth overlap of the overlapping end 54 of outer wall 59 and the outer wall 67 of adjacent turn 63 of the helically wound unit profile. The smooth curvature of curve 64 also allows when necessary the overlapping end 54 to ride up the outer surface of the curve, and the inner surface of the curve to ride up when necessary over the outer surface of hooking wall 55. It can be seen therefore that the unit profile shown in FIGS. 7 and 8 substantially maintains the insulative helical passageway 47 in the humidifier conduit, while allowing substantial flexibility in the conduit due to the armadillo-like effect of the overlapping scales or plates.

The conduits of FIGS. 3 to 8 have been shown including in each unit profile 62 heater wires 31 and 32. It is possible however that the unit profile could be formed using only one of the heater wires, and still provide a full loop of heater wire. Accomplishment of this would require that, rather than helically winding only a single axially extensive unit profile, instead two axially extensive unit profiles, each having one heater wire, would be simultaneously wound to form effectively a double helix. The bonding of adjacent turns of the axially extensive unit profiles would be identical to that required when forming the conduit by helical winding of only a single unit profile.

The process of helically winding the unit profile can be achieved in continuous process with the extrusion of the unit profile, for example by attaching the free end of the extruded profile to a cylindrical member 65, and rotating the cylindrical member 65 to form turns of the axially extensive unit profile thereon. It is preferably in this respect that cylindrical member 65 be moved in an axial direction 77 so that turns are formed on the cylindrical member in an adjacent sequence. For the embodiments of the unit profiles shown in FIGS. 5 and 7, having connection means 51 and 55, forming guides for example 73 and 74 are preferably provided adjacent the point where the unit profile is being laid on cylindrical member 65, to cause the engagement of the engagement means. Similar forming members may also be provided for the unit profile of FIG. 3, to ensure sufficient pressure for strong adhesive bonding of adjacent turns of the unit profile.

Referring to FIGS. 1 to 9, in use, the heater wires 31 and 32 are on occasion (when determined by the control means 38 within the humidifier 1) energised such that current will flow in the resistive heater wires and heat will be produced. This heat is conducted through the internal wall of the humidifier conduit. As the gas flowing within the conduit is in contact with the inner surface of the internal wall of the conduit, heat is transferred to the gases flow so that the temperature of the inner surface of the internal wall is comparable to the temperature of the humidified gases flow resulting in little or no condensation.

Referring to FIG. 2, the air pocket 36 acts as an insulating layer or buffer zone so that the heat produced by the heater wire 31 or 32 is not easily dissipated away to the ambient air. As, in reality each of the alternate air pockets are connected, the "air pocket" is actually a helical tube around the inner conduit 35 which is heated by the heater wire encouraging even heat distribution along the length of the conduit.

As the heater wire 31 or 32 is at the base of the grooves 29 in the outer surface of the inner conduit 35 the temperature on the inner surface of the inner conduit 35 at the point adjacent the heater wires will be slightly higher than the temperature on the inner surface of the inner conduit 35 adjacent the ridges 28 (which are the furthest points from the heater wires). The insulating air pockets 33 and 36 aid in minimising this temperature difference as the heated air within the pockets encourages even heat distribution around the groove and through all points of the walls of the grooves.

Referring to FIGS. 2 to 9, the insulating air layer contained between the outer and inner walls of the humidifier conduit substantially reduce the heat loss from the gases flow.

The construction and arrangement of conduit 13 is in each case identical to the previously described conduit 11.

The present invention has been found to provide an extremely flexible yet durable conduit suitable for use in a wide range of ambient temperature and draught conditions. Because of the double helical construction the conduit is able to be bent without kinking which would otherwise impede the flow of gases within the conduit. A major advantage is the ability of the present invention to minimise or reduce the temperature gradient both through and along the inner surface of the inner conduit 35 minimising or eliminating condensation.

We claim:
1. A conduit for carrying humidified gases comprising:
   at least one axially extensive unit profile helically wound with adjacent turns touching to define an axial passage within said helix, said unit profile when helically wound, with adjacent turns touching, defining at least one enclosed helical passage, around said axial passage said unit profile including a face which is disposed inwardly with said unit profile helically wound, said inwardly disposed face defining the wall of said axial passageway and sealing said axial passage from said enclosed helical passage, each turn of said helically wound profile bonded to adjacent turns of said profile.

2. A conduit as claimed in claim 1 wherein said unit profile comprises a substantially rectangular tube, said substantially rectangular tube having a longitudinal passage disposed therein, and having four substantially exteriorly flat walls, two opposing walls of each turn of said helically wound tube bonded to the adjacent walls of adjacent turns, said inwardly disposed face extending between said opposed walls.

3. A conduit as claimed in claim 2 wherein said two opposing bonded walls of said unit profile are thicker than the two opposing walls of said tube forming the interior and exterior surface of said conduit for carrying humidified gases.

4. A conduit as claimed in claim 1 wherein said unit profile includes a first connector means associated with one of said bonding sides, and a second complementary connection means engagable with said first connector means, on said other bonding side, for each turn of said helically wound tube, said first connector means being engaged with the second connector means of an adjacent turn and said second connector means being engaged with the first connector means of the other adjacent turn.

5. A conduit as claimed in claim 4 wherein said first connector means comprise a male protruding member, and said second connector means comprise a female receiving recess, complementary to said male protruding member.

6. A conduit for carrying humidified gases comprising:
at least one axially extensive unit profile helically wound with adjacent turns touching to define an axial passage within said helix, said unit profile when helically wound, with adjacent turns touching, defining at least one enclosed helical passage, around said axial passage each turn of said helically wound profile bonded to adjacent turns of said profile said unit profile including at least one heating means longitudinally disposed therein.

7. A conduit as claimed in claim 6 wherein said conduit comprises one helically wound unit profile and said heating means comprises two wires, at least one of said wires being of high resistance.

8. A conduit as claimed in claim 6 wherein said unit profile includes a male protruding member associated with one of said bonding sides and a female receiving recess, complementary to said male connecting member, on said other bonding side, for each turn of said helically wound unit profile, said male protruding member being engaged with the female receiving recess of an adjacent turn and said female receiving recess being engaged with the male protruding member of the other adjacent turn, and a heatable wire is disposed in said male protruding member.

9. A conduit as claimed in claim 7 wherein the lower resistive wire is disposed in said male protruding member.

10. A conduit as claimed in claim 6 wherein said conduit comprises two helically wound axially extensive unit profiles, forming a double helix, and said heating means comprises at least one electrically resistive wire.

11. A conduit as claimed in claim 10 wherein at least one said at least one resistive wire is disposed in said male protruding member.

12. A conduit for carrying humidified gases comprising:
at least one axially extensive unit profile helically wound with adjacent turns touching to define an axial passage within said helix, said unit profile when helically wound, with adjacent turns touching, defining at least one enclosed helical passage, around said axial passage each turn of said helically wound profile bonded to adjacent turns of said profile,
said axially extensive unit profile further comprising an inner wall, an outer wall parallel to said inner wall, and a connecting wall perpendicular to said inner and outer walls, said inner and outer walls extending from opposite ends of said connecting wall, each turn of said helically wound unit profile bonded to one adjacent turn adjacent said connecting wall and to the other adjacent turn adjacent the free end of one of the inner and outer walls, the inner wall of said helically wound unit profile forming the inner wall of said conduit and the outer wall of said helically wound unit profile forming the outer wall of said conduit.

13. A conduit as claimed in claim 12 wherein whichever of said free ends of said inner and outer walls is not bonded to an adjacent turn of said unit profile overlaps said adjacent turn of said unit profile.

14. A conduit as claimed in claim 12 wherein the free end of said inner wall is bonded to said adjacent turn.

15. A conduit as claimed in claim 14 wherein said unit profile includes a bonding wall, parallel to said connecting wall, extending from whichever of said free end of said inner and outer walls is bonded to an adjacent turn of said unit profile, and the outer surface of said bonding wall is bonded to the outer surface of the connecting wall of an adjacent turn.

16. A conduit as claimed in claim 15 wherein said bonding member includes a first connection means, and said connecting wall includes a second complementary connection means, said first connection means engaged with the second connection means of an adjacent turn.

17. A conduit as claimed in claim 16 wherein said first connection means comprises the free end of said bonding member, and said second connection means comprises a hook wall extending from the outside surface of said connecting wall to hook over said free end of said bonding wall.

18. A conduit as claimed in claim 12 wherein said unit profile includes at least one heating means.

19. A conduit as claimed in claim 18 wherein said heating means comprise electrically resistive wires.

20. A conduit as claimed in claim 17 wherein at least one heating means is disposed at or adjacent the free end of said bonding member.

21. A conduit for carrying humidified gases comprising:
an inner conduit defining the gases flow passage,
an outer conduit co-axially located with respect to said inner conduit, said outer conduit spaced radially outwardly from said inner conduit, thereby enclosing said inner conduit,
at least one intermediate co-axial helical wall disposed between said inner conduit and said outer conduit, said inner conduit, said outer conduit and said intermediate wall together defining at least one helical passage around said inner conduit, said helical passage located outside said inner conduit and inside said outer conduit,
and a heater element disposed between said inner conduit and said outer conduit and spiraling around said inner conduit.

22. A conduit as claimed in claim 21 wherein said intermediate coaxial helical wall is an elongate narrow member wound helically about said inner conduit.

23. A conduit as claimed in claim 22 wherein said elongate narrow member has a groove disposed axially therein, said member located with said groove adjacent said inner conduit, and said heater element is disposed in said groove.

24. A conduit as claimed in claim 23 wherein a wire of substantially less electrical resistance than said heater element is disposed in said helical passage around said inner conduit.

25. A conduit as claimed in claim 21 wherein at least two said intermediate co-axial helical walls are disposed between said inner conduit and said outer conduit, said outer conduit, said intermediate walls and said inner conduit defining at least two helical passages around said inner conduit, and an electrically conductive element is disposed in each of said two helical passages, at least one of said electrically conductive elements of sufficient resistance to give off heat when energized, said sufficiently resistive electrically conductive element being said heater element.

26. A conduit for carrying humidified gases comprising:
an inner conduit defining the gases flow passage,
an outer conduit co-axially located with respect to said inner conduit, said outer conduit spaced radially outwardly from said inner conduit, thereby enclosing said inner conduit, an intermediate co-axially located intermediate conduit, having at least one helical corrugation, is located between said inner conduit and said outer conduit, the outwardly disposed surface of the peaks of said at least one helical corrugation contacting the inner surface of said outer conduit, and the inwardly disposed surface of the troughs of said at least one corrugation contacting the outer surface of said inner conduit.

27. A conduit as claimed in claim 26 wherein said intermediate conduit has two said helical corrugations arranged as a double helix, and each said electrically conductive element is disposed in the trough of a respective said corrugation.

28. A conduit as claimed in claim 26 wherein said intermediate conduit is thicker than both said inner and outer walls.

* * * * *